United States Patent [19]

Schmidt et al.

[11] 4,360,669
[45] Nov. 23, 1982

[54] PREPARATION OF N-(D)-RIBITYL-2-PHENYLAZO-4,5-DIMETHYLANILINE

[75] Inventors: Wolfram Schmidt, Friedelsheim; Joachim Paust, Neuhofen; Axel Nürrenbach, Gruenstadt, all of Fed. Rep. of Germany

[73] Assignee: BASF Aktiengesellschaft, Fed. Rep. of Germany

[21] Appl. No.: 286,601

[22] Filed: Jul. 24, 1981

[30] Foreign Application Priority Data

Aug. 8, 1980 [DE] Fed. Rep. of Germany ....... 3030054

[51] Int. Cl.³ .......................... C07H 1/00; C07H 1/06
[52] U.S. Cl. ................................. 260/207.5; 127/29; 127/58
[58] Field of Search ............................ 127/29, 42, 58; 426/658; 536/19, 18, 55, 22

[56] References Cited

U.S. PATENT DOCUMENTS 2,261,608 11/1941 Tishler et al. ........................ 536/19
2,429,244 10/1947 Spiegelberg ......................... 536/18
2,847,413 8/1958 Folkers et al. ....................... 536/19

FOREIGN PATENT DOCUMENTS 168083 4/1951 Austria .
535265 1/1957 Canada ................................ 536/19
39-666564 7/1964 Japan .

OTHER PUBLICATIONS

W. H. Sebrell and R. S. Harris, "The Vitamins; Chemistry, Physiology, Pathology, Methods", 2 Edition, vol. V, 1972, Academic Press, pp. 19–26, (particularly p. 22, 2nd paragraph).
Helvetica Chimica Acta, vol. 18, (1935), pp. 1130–1134.
Helvetica Chimica Acta, vol. 19, (1936), pp. 264–269.

*Primary Examiner*—Kenneth M. Schor
*Attorney, Agent, or Firm*—Keil & Witherspoon

[57] ABSTRACT

A process for the preparation of N-(D)-ribityl-2-phenylazo-4,5-dimethylaniline (I), wherein
1. in the case of pure or virtually pure (D)-ribose (III)
   (a) the latter is reacted with 3,4-dimethylnitrobenzene (IVa) or 3,4-dimethylaniline (IVb) and with hydrogen in the presence of a hydrogenation catalyst,
   (b) the resulting solution is reacted, in a conventional manner, with an acid phenyldiazonium salt solution (VI) and
   (c) the resulting product is isolated by crystallization, in a conventional manner, or
2. in the case of crude ribose, ie. industrial mixtures of (D)-ribose and other sugars
   (a) the crude ribose is reacted with about equimolar amounts, based on III, of 3,4-dimethylaniline (IVb) and boric acid,
   (b) the boric acid ester of the Schiff base obtained from III and IVb is allowed to crystallize out and is separated off,
   (c) this ester is hydrogenated with hydrogen in the presence of a hydrogenation catalyst,
   (d) the solution is freed from catalyst and reacted, in a conventional manner, with an acid phenyldiazonium salt solution and
   (e) the resulting product I is isolated by crystallization in a conventional manner.

2 Claims, No Drawings

4,360,669

PREPARATION OF N-(D)-RIBITYL-2-PHENYLAZO-4,5-DIMETHYLANILINE

The present invention relates to an improved process for the preparation of N-(D)-ribityl-2-phenylazo-4,5-dimethylaniline (I)

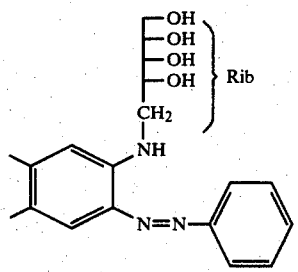

an important intermediate for the preparation of vitamin B$_2$ (riboflavin, II)

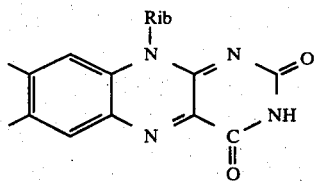

Japanese Laid-Open Application 6665/64 discloses reacting pure (D)-ribose (III) and 3,4-dimethylnitrobenzene (IVa) or 3,4-dimethylaniline (IVb) with hydrogen in the presence of palladium or Raney nickel, to give 3,4-dimethyl-N-(D)-ribitylaniline (V), which can then be converted to (I) with phenyldiazonium chloride (VI) in a conventional manner.

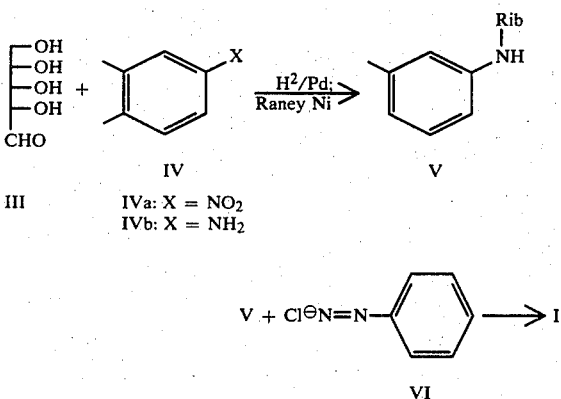

However, industrial operation of this process presents considerable problems, since on the one hand pure (D)-ribose has not hitherto been obtainable at economically justifiable expense by epimerization of arabinose, whilst on the other hand (V) can only be isolated with difficulty from the reaction mixtures obtained when using technical-grade ribose (ie. crude ribose of about 50–70% purity). Since the isomeric sugars contained in crude ribose, in the main D-arabinose (VII), react similarly with IV, losses of the valuable starting materials (IV) additionally occur.

Such losses also arise in the process of Austrian Pat. No. 168,083, in which crude ribose, containing about 50% of arabinose, is reacted with IVb and boric acid to give the boric acid ester of the Schiff base of IVb and III. This boric acid ester can be isolated in a pure form from the reaction mixture, thus obtained, by crystallization. The crystals are separated off, dried, redissolved in water or water/alcohol and hydrogenated to give V. Thereafter, V is isolated by crystallization and dissolved in aqueous hydrochloric acid. The solution is purified with active charcoal, after which V is again crystallized out. An aqueous solution of the pure V is then subjected to azo coupling with VI, after which product I is isolated by crystallization.

Though I can be obtained in a pure form in this way, the process is not useful industrially, because of the losses of IVb and because of the numerous individual operations involved.

It is an object of the present invention to provide a method whereby I can be prepared in a technically more simple, and more economical, method from pure ribose or from crude ribose.

We have found that this object is achieved and that N-(D)-ribityl-2-phenylazo-4,5-dimethylaniline (I) is obtained by a method wherein 1. in the case of pure or virtually pure (D)-ribose (III)
   (a) the latter, in aqueous or aqueous-organic solution, or in solution in a water-soluble organic solvent, is reacted, at from 20° to 100° C., with 3,4-dimethylnitrobenzene (IVa) or 3,4-dimethylaniline (IVb) and hydrogen, under a hydrogen pressure of from 10 to 100 bar, in the presence of a hydrogenation catalyst,
   (b) the resulting solution is reacted direct or after removing the organic solvent in a conventional manner with an acid phenyldiazonium salt solution (VI) and
   (c) the resulting product is isolated by crystallization in a conventional manner, or 2. in the case of crude ribose, ie. an industrial mixture of (D)-ribose and other sugars
   (a) the crude ribose, in aqueous or aqueous-organic solution or in solution in a water-soluble organic solvent, is reacted, at from 0° to 50° C., with about equimolar amounts, based on III, of 3,4-dimethylaniline (IVb) and boric acid,
   (b) the boric acid ester of the Schiff base obtained from III and IVb is allowed to crystallize out and is separated off,
   (c) the boric acid ester is hydrogenated, in aqueous or aqueous-organic solution, at from 20° to 70° C. and under a hydrogen pressure of from 10 to 100 bar, with hydrogen in the presence of a hydrogenation catalyst,
   (d) the solution is freed from catalyst and reacted, in a conventional manner, with an acid phenyldiazonium salt solution and
   (e) the resulting product I is isolated by crystallization in a conventional manner.

Particularly noteworthy features of this process are that in the case of pure ribose (process steps 1a–1c), hydrogenation and azo coupling can—contrary to previous concepts—be effected in the same reaction medium, without isolating the intermediates, and that in the case of crude ribose (process steps 2a–2e), only about equimolar amounts, based on ribose content, of the expensive compound 3,4-dimethylaniline (IVb) are required, this being an essential aspect in order to make the use of crude ribose economical at all. Furthermore, in this case, again, the azo coupling can follow directly onto the hydrogenation of the boric acid ester of the Schiff base of III and IVb, without isolation of the intermediate V.

These advantages result in a considerable simplification of the synthesis of I and hence of vitamin $B_2$ (II), and very particularly so where crude ribose is used.

The individual steps of both versions of the process will be explained in more detail below.

1. Use of pure ribose as the starting material Process step (1a)

In this step, pure or virtually pure (D)-ribose (III) is reacted with about equimolar amounts of 3,4-dimethylnitrobenzene (IVa) or 3,4-dimethylaniline (IVb) under hydrogenating conditions. Since IVb is prepared from IVa, the use of the nitro compound IVa is of course preferred.

Accordingly, the following reactions take place under the reaction conditions employed:

reduction of IVa to IVb by hydrogenation (not applicable if IVb is used as the starting material), condensation of III with IVb to give the Schiff base and hydrogenation of the Schiff base to give the amino compound V.

Suitable reaction media are water, methanol, ethanol and aqueous-organic solutions, especially those comprising from 20 to 80% by volume of water and from 80 to 20% by volume of methanol or ethanol. The economically optimum amount, which is from about 4 to 40 liters per kg of III, can readily be determined in a conventional manner by a few preliminary experiments.

Advantageously, this reaction is carried out at from 30° to 100° C. and under a hydrogen pressure of from 10 to 100 bar.

Suitable hydrogenation catalysts are, in particular, palladium/charcoal and Raney nickel, and these are used in the amounts conventionally employed for such hydrogenations (from about 10 to 100 g of Pd or 100–300 g of Raney nickel per kg of III).

This process step requires from about 1 to 3 hours under the preferred reaction conditions, and gives V in yields of about 85–95%.

Process step (1b)

After removing the hydrogenation catalyst, the resulting solution of V is reacted, direct or after removing the organic solvent, with a phenyldiazonium salt solution (VI) at from −5° to 5° C. To avoid handling substantial volumes of liquid, the solution can however be concentrated beforehand to the point where V starts to precipitate.

The diazonium salt solution can be prepared in a conventional manner from aniline, Na nitrite or K nitrite and an aqueous acid. In general, hydrochloric acid is used, since it is inexpensive, but it is also possible to use, for example, sulfuric acid. Further, it is advantageous to have acetic acid or Na acetate present. The pH in this reaction is advantageously from 1 to 2.

Process step (1c)

After azo coupling, the product I is isolated by crystallization in a conventional manner and washed with water and a water-soluble solvent, for example with methanol. The purity of I is in general adequate for further conversion to vitamin $B_2$. If required, however, the product can be recrystallized, for example from methanol or ethanol.

The yield, based on ribose or on compound IVa or IVb, is from about 76 to 81%.

Process step (2a)

Our observations to date indicate that crude ribose of any origin can be used for the process according to the invention. Crude ribose obtained by conventional processes of manufacture contains, in addition to (D)-ribose, 30–50% of other compounds, in the main isomeric pentoses and especially (D)-arabinose. If pure (D)-ribose, an expensive material, were used, the presence of boric acid as an aid to the preparation of pure I would in theory be unnecessary when following process version 1. Since, however, physiological active compounds must conform to extremely stringent purity standards, the rule is that this requirement can most readily be met by carrying out the synthesis via intermediates which are each very pure. For this reason, version 2 of the process according to the invention offers advantages even if the ribose employed is only slightly impure, since proceeding via the boric acid ester permits removal of by-products in any case.

In industry, however, at least where ribose is prepared by epimerization of D-arabinose, it is only crude ribose which need be considered. The crude ribose described in Austrian Pat. No. 168,083 and obtainable by amalgam reduction of ribonolactam is also a suitable starting material.

Currently the most important industrial crude ribose contains about 70% of (D)-ribose and is obtained by epimerizing (D)-arabinose by the method of Bilek (Czech Pat. No. 149,472), using molybdic acid.

If the ribose is to be fully utilized, the molar amount of 3,4-dimethylaniline (IVb) should correspond to the ribose content of the crude ribose.

The boric acid is advantageously used in amounts of from 0.7 to 1 mole per mole of ribose. It is possible first to esterify the ribose with boric acid and then carry out the reaction with IV, but in general it is advisable to treat the ribose simultaneously with boric acid and IV.

The boric acid ester of the Schiff base is sparingly soluble in the aqueous or aqueous-organic medium, and can therefore be made to crystallize virtually completely, if necessary after cooling the reaction mixture. Suitable solvents, as in the case of process step (1a), are water, methanol and ethanol, and water-methanol and water-ethanol mixtures in the proportions stated earlier.

Preferably, process step (2a) is carried out at from 30° to 50° C. The reaction time at these temperatures is from about 0.2 to 1 hour.

Process step (2b)

After completion of the reaction, the boric acid ester is advantageously allowed first to crystallize out partially, by gradual temperature lowering, and then to crystallize out completely at a lower temperature, from about 0° to 20° C. The crystals are separated off and are advantageously used further while moist. Washing of the crystals to remove excess IVb can be useful; such washing can be carried out with, for example, methylene chloride or ether.

Process step (2c)

To hydrogenate the boric acid ester of the Schiff base, the ester is advantageously dissolved in a 5–10-fold amount of water or of an aqueous organic solvent, for example methanol/water or ethanol/water. As regards the type and optimum amount of solvent, the remarks made in connection with process step (1a) again apply, and this is also true of the other hydrogenation conditions, though the temperature should not exceed 70° C.

Process step (2d)

After removing the hydrogenation catalyst, the resulting solution of the boric acid ester of V can, as in process step 1b, be reacted, direct or after removal of the organic solvent, with a phenyl-diazonium salt solution at from −5° to 5° C. Under the conditions of this reaction, the boric acid is split off again.

Process step (2e)

This process step corresponds to process step (1c).

The yields, based on the ribose content of the crude ribose, depend on the nature of the latter and are from about 75 to 80%; according to our observations to date, the best values are achieved with the crude ribose obtained by the Bilek process, ie. by epimerizing arabinose with molybdic acid.

EXAMPLE 1

Preparation of I from pure ribose 21 g (140 millimoles) of ribose (III) and 21.1 g (140 millimoles) of 3,4-dimethylnitrobenzene were dissolved in a mixture of 45 ml of water and 45 ml of methanol and hydrogenated under 80 bar hydrogen pressure at 55° C. in the presence of 7 g of Raney nickel. The yield of 3,4-dimethyl-N-ribitylaniline was 90%.

The catalyst and the methanol were removed from the solution, after which the latter was mixed with 100 ml of concentrated hydrochloric acid and 40 ml of acetic acid.

This solution was then reacted, at 0° C. and pH 1, with a phenyldiazonium chloride solution which had been prepared from 12.4 g (133 millimoles) of aniline, 9.1 g of NaNO$_2$ and 100 ml of 15% strength by weight hydrochloric acid at −5° C.

After completion of azo coupling, the pH was brought to 3 with NaOH, whereupon (I) crystallized out. The yield of N-ribityl-2-phenylazo-4,5-dimethylaniline was 80%, based on ribose employed.

EXAMPLE 2

Preparation of I from crude ribose

The crude ribose used was obtained by Bilek epimerization of (D)-arabinose, as follows 100 g of (D)-arabinose in 500 ml of water were heated with 1 g of molybdic acid for 3 hours at 90°–100° C. The aqueous solution was evaporated down and the mixture which remained was dissolved, at 65° C., in 230 ml of a mixture of 90% by volume of ethanol and 10% by volume of water, after which the solution was cooled. Hereupon, 70 g of arabinose crystallized out. The mother liquor contained 70% pure crude ribose, ie. 21 g (140 millimoles) of ribose (III) and 9 g of other sugars.

This solution was then concentrated to about 100 ml and 16.9 g (140 millimoles) of 3,4-dimethylaniline (IVb) and 12.4 g (200 millimoles) of boric acid were added at 45° C. When a clear solution had formed, it was cooled to 20° C., whereupon the boric acid ester of the Schiff base of III and IVb began to crystallize out. After 2 hours, the crystallization was completed by allowing a further 2 hours, but at 0° C. The crystals were filtered off and washed with ether. The yield of the boric acid ester was 90%, based on III.

The crystals, while still moist, were then dissolved in a mixture of 270 ml of methanol and 15 ml of water and hydrogenated in the presence of 11 g of Raney nickel at 55° C. and 30 bar hydrogen pressure. The yield of 3,4-dimethyl-N-ribitylaniline was 95% (corresponding to 30.5 g = 120 millimoles).

The solution obtained from the hydrogenation step was concentrated to about 50 ml and 100 ml of concentrated hydrochloric acid and 40 ml of acetic acid were then added.

A phenyldiazonium chloride solution which had been prepared in a conventional manner from 12.4 g (133 millimoles) of aniline and 9.1 g of NaNO$_2$ in 90 ml of 15% strength by weight hydrochloric acid was then added at −5° C. The pH was from 1 to 1.5. After completion of coupling, the pH was brought to 3.5 with NaOH, whereupon product I crystallized out. The crystals were separated off and washed with water. The yield of I was 90% in respect of the coupling reaction, and 77% based on ribose employed.

We claim:

1. A process for the preparation of N-(D)-ribityl-2-phenylazo-4,5-dimethylaniline from crude ribose, as an industrial mixture of (D)-ribose and other sugars, which process comprises:

(a) reacting the crude ribose, while in aqueous or aqueous-organic solution or while in solution in a water-soluble organic solvent at from 0° to 50° C., with about equimolar amounts, based on (D)-ribose, of 3,4-dimethylaniline and boric acid;

(b) crystallizing the boric acid ester of the Schiff base obtained, which ester was obtained in step (a), and separating the boric acid ester crystals from solution;

(c) dissolving the boric acid ester crystals in aqueous or aqueous-organic solution;

(d) hydrogenating the solution of boric acid ester obtained by step (c) at from 20° to 70° C., under hydrogen, at a pressure of from 10 to 100 bar, in the presence of a hydrogenation catalyst;

(e) separating the solution from the catalyst and reacting the N-(D)-ribityl-3,4-dimethylaniline resulting from step (c) while still in solution in a conventional manner with an acid phenyldiazonium salt solution; and (f) isolating the resulting product by crystallization in a conventional manner.

2. A process as claimed in claim 1 wherein the crude ribose employed has been obtained by epimerizing arabinose with molybdic acid.

* * * * *